(12) United States Patent
Kieval

(10) Patent No.: US 6,178,349 B1
(45) Date of Patent: Jan. 23, 2001

(54) DRUG DELIVERY NEURAL STIMULATION DEVICE FOR TREATMENT OF CARDIOVASCULAR DISORDERS

(75) Inventor: Robert S. Kieval, Golden Valley, MN (US)

(73) Assignee: Medtronic, Inc., Minneapolis, MN (US)

( * ) Notice: Under 35 U.S.C. 154(b), the term of this patent shall be extended for 0 days.

(21) Appl. No.: 09/292,507

(22) Filed: Apr. 15, 1999

(51) Int. Cl.$^7$ ..................................................... A61N 1/36
(52) U.S. Cl. ................................ 607/3; 607/118; 607/120
(58) Field of Search ........................ 607/115–118, 120, 607/3; 600/372, 373, 377; 604/93, 20, 113, 118, 131, 132, 141, 151, 181, 65–67, 264

(56) References Cited

U.S. PATENT DOCUMENTS

| | | | |
|---|---|---|---|
| 4,573,481 | 3/1986 | Bullara et al. | 128/784 |
| 4,590,946 | 5/1986 | Loeb | 128/642 |
| 4,602,624 | * 7/1986 | Naples et al. | 607/118 |
| 4,649,936 | 3/1987 | Ungar et al. | 128/784 |
| 5,038,781 | 8/1991 | Lynch | 128/419 |
| 5,199,428 | 4/1993 | Obel et al. | 128/419 |
| 5,265,608 | 11/1993 | Lee et al. | 126/642 |
| 5,282,468 | 2/1994 | Klepinski | 128/642 |
| 5,313,953 | 5/1994 | Yomtov et al. | 128/696 |
| 5,344,438 | 9/1994 | Tresterman et al. | 607/118 |
| 5,388,578 | 2/1995 | Yomtov et al. | 128/642 |
| 5,400,784 | 3/1995 | Durand et al. | 128/642 |
| 5,411,031 | 5/1995 | Yomtov | 128/706 |
| 5,505,201 | 4/1996 | Grill et al. | 128/642 |
| 5,824,027 | * 10/1998 | Hoffer et al. | 607/118 |

OTHER PUBLICATIONS

Clinical Studies On Varatrum Alkoids (The Action of Protoveratrine and Veratridine in Hypertension) By Edward Meiman M.D. and Otto Krayer M.D. (pp. 204–213) Circulation 1950.
U.S. Patent application Ser. No. 08/559,957 Entitled Baroreflex Modulation with Carotid Sinus Nerve Stimulation for the Treatment of Heart Failure By Robert S. Kieval et al.
Reversal of Reflex–Induced Myocardial Ischemia by Median Nerve Stimulation a Feline Model of Electroacupunture By Peng Li et all (pp. 1186–1194) Circulation.

* cited by examiner

Primary Examiner—Jeffrey R. Jastrzab
(74) Attorney, Agent, or Firm—Michael B. Atlass; Harold R. Patton (57) ABSTRACT

An implantable medical device for treatment of cardiovascular disorders by stimulating a selective nerve, the device including an implantable pulse generator, an implantable electrode body and a reservoir. The electrode body includes an electrode electrically connected to the pulse generator. Further, the electrode body is configured to sustain long-term contact between the electrode and the nerve. The reservoir maintains a nerve stimulating drug, such as a veratrum alkaloid, and defines a delivery surface through which the drug is released from the reservoir. Finally, the reservoir is operatively associated with the electrode body to deliver the nerve stimulating drug directly to the nerve. During use, the electrode and the delivered drug stimulate the nerve to effect control over the cardiovascular system of the patient.

33 Claims, 5 Drawing Sheets

DRUG DELIVERY NEURAL STIMULATION DEVICE FOR TREATMENT OF CARDIOVASCULAR DISORDERS

BACKGROUND OF THE INVENTION

The present invention concerns a system for treating a cardiovascular disorder by artificial neural stimulation. More particularly, it relates to an implantable medical device configured to provide both chemical and electrical stimulation of one or more nerves of a patient, causing regulation of the heart, vasculature and other bodily systems.

A variety of different cardiovascular ailments relate to, or are caused by, abnormal blood pressure regulation. In general terms, the heart functions to pump blood containing oxygen and nutrients to bodily tissues and organs. Blood being pumped to and from the heart develops a pressure (or blood pressure) in the heart and arteries. Blood pressure is determined by cardiac output and peripheral vascular resistance. The cardiac output, in turn, is a function of heart rate and stroke volume.

Given the above, treatment of abnormal blood pressure-related cardiovascular disorders, such as hypertension and congestive heart failure, focus upon adjusting heart rate, stroke volume, peripheral vascular resistance, or a combination thereof. With respect to heart rate, one area of particular interest is vagal control. The rate of the heart is restrained by vagus nerves in conjunction with cardiac depressor nerves. The vagus nerves extend from the medulla and innervate the heart (as well as other organs). The medulla, in turn, regulates sympathetic and parasympathetic nervous system output, and can affect heart rate in part by controlling vagus nerve activity (or vagal tone) to the heart. The medulla exerts this autonomic control over the heart in response to sensed changes in blood pressure. More particularly, a series of pressure sensitive nerve endings, known as baroreceptors, are located along the carotid sinus, a dilated area at the bifurcation of the common carotid artery. The baroreceptors are formed at the terminal end of the carotid sinus nerve (or Hering's nerve), which is a branch of the glossopharyngeal nerve. The glossopharyngeal nerve extends to the medulla such that the carotid sinus baroreceptors communicate (or signal) with the medulla with carotid sinus pressure information. A reflex pathway (or baroreflex) is thereby established, with the medulla automatically causing an adjustment in heart rate in response to a pressure change in the carotid sinus. For example, a rise in carotid sinus pressure causes the medulla to increase vagal neuronal activity. The above-described reflex pathway (or baroreflex) results in a lowering of the heart rate, and therefore blood pressure. A similar relationship is found with myocardial baroreceptors on the aortic arch. Notably, bodily systems other than the heart, such as the systemic vasculature and kidneys, are also influenced by nerve stimulation and contribute to overall cardiovascular regulation. In light of this vagally-mediated, baroreflex control of heart rate and other bodily systems, it may be possible to regulate heart rate, and thus blood pressure, by artificially stimulating the carotid sinus nerves, myocardial nerves, or other cardiovascular influencing nerves.

One available technique for providing artificial neural stimulation entails implanting an electrode into direct contact with a portion of a selected nerve. A separate, battery-powered activation source or triggering device is likewise implanted and connected to the electrode. The electrode is periodically activated by the triggering device, thereby stimulating the nerve in question and prompting a baroreflex decrease in heart rate. Essentially, activation of the electrode serves to simulate a rise in blood pressure, causing the baroreflex reduction in heart rate. One example of an implantable electrical nerve stimulator is provided in U.S. Pat. No. 5,199,428 assigned to Medtronic, Inc. of Minneapolis, Minn.

While electrical neural stimulation has proven to be a highly viable therapy, certain disadvantages may arise. For example, the battery associated with the triggering device has a finite life, and will inevitably require replacement. Further, in order to achieve adequate nerve stimulation, the frequency, amplitude and/or duration of electrode activation may rise to a level whereby surrounding muscle tissue is also affected, potentially leading to patient discomfort. Finally, it is possible that the nerve will become "desensitized" to the electrical stimulation, requiring increased activation levels and/or duration's, again contributing to patient discomfort and reduced battery life.

As an alternative to electrical stimulation, efforts have been made to identify acceptable chemical compounds formulated to artificially prompt baroreflex control of heart rate, vasculature and other bodily systems. One potentially applicable class of compounds is veratrum alkaloids. Veratrum alkaloids constitute a large group of steroid-like polycyclic nitrogen-containing ring structures found in any of the veratrum species. Two known preparations of veratrum are "veratrum viride" from Veratrum viride, and "veratrum album" from Veratrum album. Further research has identified certain other veratrum alkaloids, such as protoveratrine and veratridine, as being more capable of eliciting the reflex decrease in heart rate and blood pressure. Meilman, E., et al., "Clinical Studies On Veratrum Alkaloids", *Circulation* 1:204–213 (1950). Meilman et al. and others have described systemic delivery of the veratrum alkaloid for prompting baroreflex actions. While use of veratrum alkaloids originally appeared quite promising, numerous deleterious side effects associated with systemic application of the compound, such as nausea and severe hypotension, rendered the therapy minimally useful. In short, compound toxicity and related side effects have limited clinical utility of veratrum alkaloids.

Treatment of cardiovascular disorders characterized by increased heart rate or blood pressure, such as hypertension or congestive heart failure, by neural stimulation presents a highly viable therapy. To this end, while electrical stimulation via an implanted electrode is effective, certain potential disadvantages have been identified. Alternatively, systemic delivery of chemical nerve stimulators, and in particular veratrum alkaloids, has been problematic. Therefore, a substantial need exists for a neural stimulation device configured to deliver a nerve stimulating drug, such as veratrum alkaloid, directly to a nerve in conjunction with electrical nerve stimulation.

SUMMARY OF THE INVENTION

One aspect of the present invention provides an implantable medical device for enhanced stimulation of a nerve of a patient to treat cardiovascular disorders. The device includes an implantable pulse generator, an implantable electrode body and a reservoir. The electrode body includes an electrode electrically connected to the pulse generator. The electrode body is configured to sustain long-term contact between the electrode and the nerve following implant. The reservoir maintains a nerve stimulating drug. In this regard, the reservoir defines a delivery surface through which the drug is released from the reservoir. Finally, the reservoir is operatively associated with the electrode body to deliver the nerve stimulating drug via the delivery surface to the nerve following implant. During use, the electrode and the drug released from the reservoir act to stimulate the nerve, effecting cardiovascular regulation. In one preferred embodiment, the nerve stimulating drug is a veratrum alkaloid. In another preferred embodiment, the reservoir is controlled to selectively deliver the veratrum alkaloid.

Another aspect of the present invention provides an improved neural stimulation device for treatment of cardiovascular disorders. The device includes an electrode body having an electrode connected to an implantable pulse generator. The electrode body is configured for implantation within a patient so as to establish long-term contact between the electrode and a selected nerve the stimulation of which affects cardiovascular activity. The improvement comprises a reservoir operatively associated with the electrode body. The reservoir maintains a nerve stimulating drug. Further, the reservoir is configured to deliver the drug directly onto the selected nerve. Once delivered, the drug stimulates the nerve, effecting an alteration in cardiovascular activity. In one preferred embodiment, the nerve stimulating drug is a veratrum alkaloid.

Yet another aspect of the present invention relates to a method for improved neural stimulation to treat cardiovascular disorders. The method includes stimulating a nerve with an electrode. The nerve is further stimulated with a nerve stimulating drug delivered from a reservoir. In this regard, the reservoir is implanted in close proximity to the nerve such that the drug is effectively directly delivered to the nerve. In one preferred embodiment, the nerve stimulating drug is a veratrum alkaloid delivered to the nerve. In another preferred embodiment, delivery of the drug is correlated with activation of the electrode to generate an overall nerve stimulation therapy.

DETAILED DESCRIPTION OF THE PREFERRED EMBODIMENTS

Figure 1:
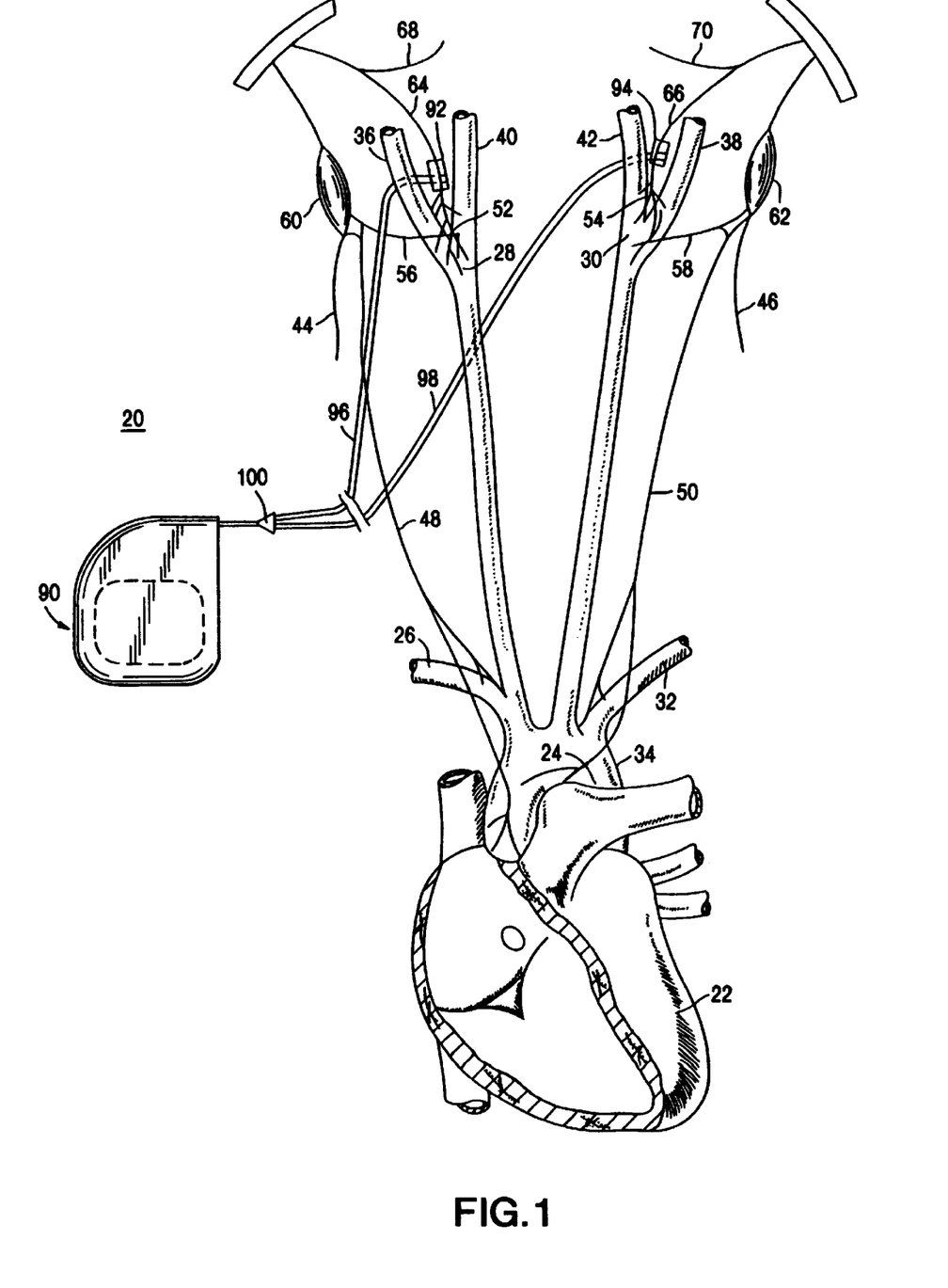
FIG. 1 is a diagrammatic illustration of the heart, its associated blood vessels and nerves, and an implantable medical device in accordance with the present invention coupled thereto.

One preferred embodiment of an implantable medical device 20 in accordance with the present invention is shown in FIG. 1. For purposes of clarity, the medical device 20 is shown in FIG. 1 in conjunction with a patient's cardiovascular system. In general terms, the cardiovascular system is focused about the heart 22 which pumps oxygenated blood out through an aortic arch 24, which leads to a right subclavian artery 26, a right common carotid 28, a left common carotid 30, a left subclavian artery 32, and a thoracic aorta 34. The body's system utilizes stretch receptors located in the atrial walls in the aortic arch 24 and at the bifurcation of the carotid arteries 28, 30 in the carotid sinus portion of the neck. The bifurcation of the carotid arteries 28, 30 leads to external carotid arteries 36, 38, respectively, and to internal carotid arteries 40, 42, respectively.

Nerve fibers extending from stretch receptors in the aortic arch 24 join the left and right vagus nerves 44, 46, respectively, with these fibers being referred to as cardiac depressor nerves 48, 50. A number of nerves extend from the stretch receptors at the bifurcation of the carotid arteries 28, 30 in the carotid sinus, with the areas immediately above the bifurcations being referred to as the carotid sinus bodies 52, 54. Nerve branches 56, 58 extend from the carotid bodies 52, 54, respectively, and join the ganglions of vagus 60, 62, respectively. Other nerve fibers comprising the carotid sinus nerve branches 64, 66 (generally referred to as "Hering's nerves") of the glossopharyngeal nerves 68, 70, respectively, also extend from the carotid bodies 52, 54, respectively, to the medulla (not shown).

The rate of the heart is restrained by the right and left vagus nerves 44, 46, respectively, in conjunction with the cardiac depressor nerves 48, 50, respectively. The cardio-inhibitory center of the nervous system exerts a tonic effect upon the heart 22, via the vagus nerves 44, 46, restraining its rate. This effect is better known as vagal tone. Selective stimulation of the right or left vagus nerves 44, 46 may bring into control the heart rate and blood flow without resorting to direct stimulation of the heart 22. With vagal stimulation, it is possible to slow the heart rate down and allow more complete cardiac relaxation. A similar reflex control of heart rate occurs by stimulation of the right or left carotid sinus nerves 64, 66, respectively. The carotid sinus nerves 64, 66 extend to the medulla and provide information related to blood pressure in the carotid sinus bodies 52, 54. Thus, stimulation of the right or left carotid sinus nerve 64, 66, respectively, simulates a rise in pressure, causing the baroreflexive reduction in heart rate. Notably, artificial neural stimulation as described above also influences other bodily systems to relating to cardiovascular activity, such as systemic vasculature and kidneys.

It should be understood that for ease of illustration, the heart, the nerves, arteries, veins and device 20 are not necessarily depicted in proper scale or proportion. The medical device 20 includes a pulse generator 90, a first nerve stimulator 92 and a second nerve stimulator 94. As described in greater detail below, the first and second nerve stimulators 92, 94 are electrically connected to the pulse generator 90 via first and second leads 96, 98, respectively, and a connector block 100.

The pulse generator 90 is of a type commonly known in the art and may include an indifferent case electrode 102. The pulse generator 90 includes internal circuitry and an electrically-activated power source for selectively activating the nerve stimulators 92, 94. The power source may assume a wide variety of forms, such as a battery, a large capacitor with a slow discharge rate, or various other mechanical devices. Further, as described elsewhere, the pulse generator 90 may include additional circuitry for sensing and interpreting cardiovascular activity, for activating and deactivating individual portions of the nerve stimulators 92, 94 and for correlating nerve stimulation operations.

The nerve stimulators 92, 94 are described in greater detail below, With reference to FIG. 1, however, the nerve stimulators 92, 94 are placed, in one preferred embodiment, about the right and left carotid sinus nerves 64, 66, respectively. It will be recalled that the carotid sinus nerves 64, 66 include baroreceptors (not shown) innervating the carotid bodies 52, 54, respectively. The specific location of the nerve stimulators 92, 94 may be varied along the carotid sinus nerves 64, 66, and it is contemplated that in the practice of the present invention it may be possible to place such stimulators at the right or left stellate ganglion 60, 62. Alternatively, the nerve stimulators may be placed about the vagus nerves 44, 46 or nerves associated with the myocardial baroreceptors. Alternatively, the device 20 may be useful as a response to ischemic conditions, such that the nerve stimulators 92, 94 are placed about the median nerves. Cardiovascular regulation via median nerve stimulation is described, for example, in Li et al., "Reversal of Reflex-Induced Myocardial Ischemia by Median Nerve Stimulation: A Feline Model of Electroacupuncture," *Circulation* 97(12), pp. 1186–94 (Mar. 31, 1998), hereby incorporated by reference. Finally, while the device 20 is shown as preferably including two nerve stimulators 92, 94, it is possible that only a single nerve stimulator need be provided.

Figure 2:
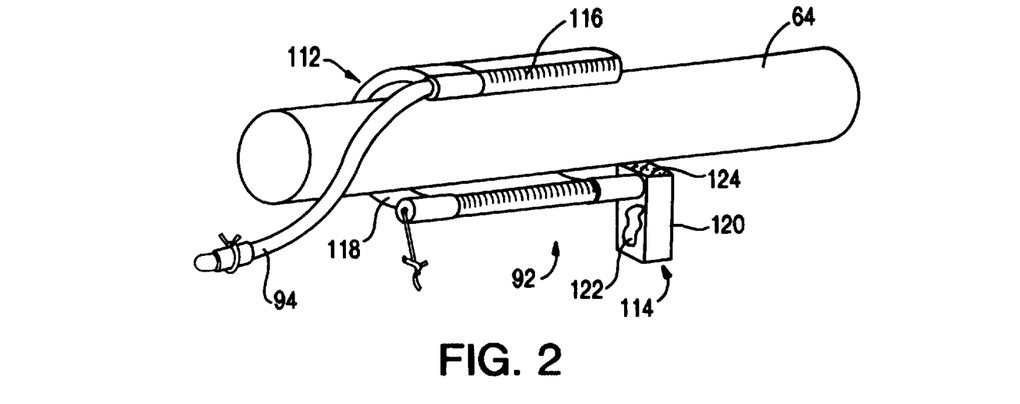
FIG. 2 is a perspective view of an electrode body and reservoir in accordance with the present invention associated with a nerve.

One preferred embodiment of the first nerve stimulator 92 is shown in FIG. 2. It should be understood that the second nerve stimulator 94 (FIG. 1) is preferably identical. The nerve stimulator 92 is shown in conjunction with a segment of the carotid sinus nerve 64, and includes an electrode body 112 and a reservoir 114. The reservoir 114 is operatively associated with the electrode body 112. Thus, upon implantation of the electrode body 112, the reservoir 114 is positioned in close proximity to the nerve 64.

The electrode body 112 is of a type commonly known in the art and includes an electrode 116 maintained by a base 118. The electrode 116 is electrically connected to the pulse generator 90 (FIG. 1) by the lead 94. The electrode 116 may take the form of a metallic foil or a conductive hydrophilic gel electrode, and may include a plurality of individual electrodes (such as a tripolar electrode). Additionally, a steroid-eluting body may be associated with the electrode 116. In one preferred embodiment, the base 118 is a substrate material, for example a flexible polymeric material, configured to sustain long-term contact between the electrode 116 and the nerve 64. To this end, as shown in FIG. 2, in one preferred embodiment, the base 118 assumes a cuff configuration so as to be wrapped about the nerve 64. Acceptable cuff configurations are well known in the art and are shown, for example, in U.S. Pat. Nos. 4,590,946; 4,573,481; 5,505,201; 5,400,784; 5,344,438; 5,282,468; 5,265,608; 5,038,781; and 4,649,936, the teachings of which are incorporated herein by reference. Alternatively, a separate attachment device may be provided, such as suture for mounting the electrode body 112 to tissue (not shown) adjacent the nerve 64.

The reservoir 114 is, in one preferred embodiment, a container 120 maintaining a nerve stimulating drug 122 (shown generally in FIG. 2). The container 120 is preferably made of a biocompatible polymeric material such as silicone, polyurethane or other commonly used materials, and defines a delivery surface 124. The delivery surface 124 is configured to permit delivery of the drug 122 from the container 120, and in one preferred embodiment is a microporous tip. With this configuration, the nerve stimulating drug 122 will be released (such as, for example, by elution) on a relatively constant basis.

In one preferred embodiment, the nerve stimulating drug 122 is a veratrum alkaloid. The veratrum alkaloid is a compound or alkaloid formed from any of the veratrum species, such as veratrum viride or veratrum album. In one preferred embodiment, the veratrum alkaloid is protoveratrine. Alternatively, but in no way limiting, the veratrum alkaloid may be veratridine. The veratrum alkaloid 122 may be formulated as a liquid, gel or solid, and may be combined with other materials to facilitate placement in the reservoir 114 and subsequent delivery. Alternatively, other nerve stimulating drugs may be employed. While the exact volume of the nerve stimulating drug 122 will vary depending upon composition and desired life of the nerve stimulator 92, the volume should not exceed five cubic centimeters for viable implantation proximate the volume should not exceed five cubic centimeters for viable implantation proximate the nerve 64. Regardless of the exact formulation, the nerve stimulating drug 122 will preferably elute from the reservoir 114 following implant.

The reservoir 114, and in particular the container 120, is preferably secured to the electrode body 112. For example, the container 120 may be secured to the base 118 with a biologically safe adhesive such as a silicone adhesive. Alternatively, the base 118 and the container 120 may be integrally formed. The reservoir 114 is orientated relative to the electrode body 112 such that upon implant, the delivery surface 124 is in close proximity to the nerve 64.

During use, and with reference to FIGS. 1 and 2, the medical device 20 is implanted within a patient. More particularly, in one preferred embodiment, the first and second nerve stimulators 92, 94 are secured to the carotid sinus nerves 64, 66, respectively. Similarly, the pulse generator 90 is implanted within the body, spaced from the nerve stimulators 92, 94. The nerve stimulators 92, 94 are connected to the pulse generator 90 via the first and second leads 96, 98, respectively, and the connector block 100. Following implant, the pulse generator 90 selectively activates the electrodes 116 associated with each of the nerve stimulators 92, 94, either individually or simultaneously. Further, a relatively constant supply of the nerve stimulating drug 122 (preferably veratrum alkaloid) is delivered to the respective nerves 64, 66, via the delivery surface 124. Stimulation of the carotid sinus nerves 64, 66 via the electrodes 116 and the drug 122 simulates a pressure rise in the carotid sinus bodies 52, 54. As a result, in one preferred embodiment, heart rate is reduced by a baroreflex operation of the cardiovascular system. Alternatively, depending upon the particular nerve being stimulated, other bodily systems related to the cardiovascular system may instead, or in addition, be controlled.

Figure 3:
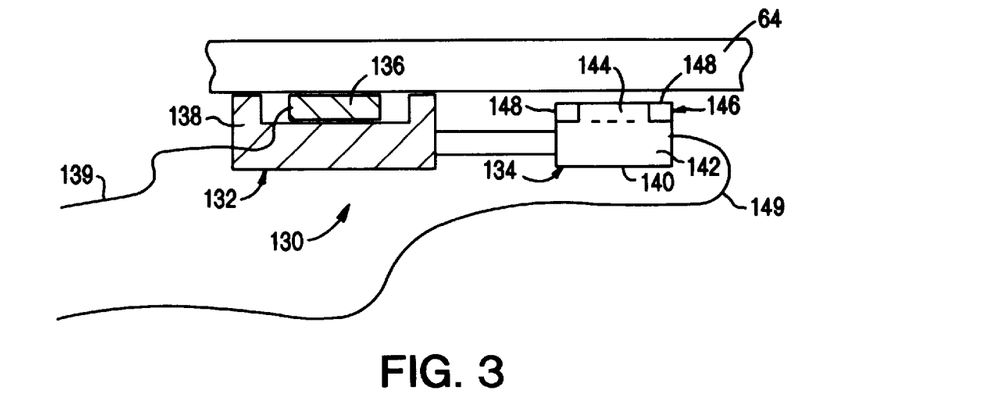
FIG. 3 is a schematic, cross-sectional view of an electrode body and alternative reservoir in accordance with the present invention associated with a nerve.

An alternative embodiment of a nerve stimulator 130 is shown in FIG. 3 in conjunction with a segment of the carotid sinus nerve 64. The nerve stimulator 130 includes an electrode body 132 and a reservoir 134. The electrode body 132 is virtually identical to the electrode body 112 previously described, includes an electrode 136 and a base 138. The base 138 is configured to sustain long-term contact between the electrode 136 and the nerve 64. The electrode 136 is electrically connected to the pulse generator 90 (FIG. 1) by a lead 139.

The reservoir 134 includes a container 140 maintaining a nerve stimulating drug 142, such as a veratrum alkaloid, as previously described. The container 140 defines a delivery surface 144 comprised of at least one opening (not shown)

through which the nerve stimulating drug 142 is released from the container 140, such as by elution of the nerve stimulating drug 142. Delivery of the nerve stimulating drug 142 through the delivery surface 144 is regulated by a regulating apparatus 146. In one preferred embodiment, the regulating apparatus 146 is an electromagnetic-based device and includes magnets 148 electrically connected to the pulse generator 90 (FIG. 1) by a lead 149. In a first, default position, the magnets 148 position a stop (not shown) over the delivery surface 144, thereby preventing release of the nerve stimulating drug 142. Conversely, in response to a signal from the pulse generator 90, the magnets 148 maneuver the stop to a second position away from the delivery surface 144. In this second position, the nerve stimulating drug 142 is readily released from the container 140. Alternatively, the regulating apparatus 146 may include a plurality of magnetic particles surrounding the container 140, which is flexible. Upon activation by the pulse generator 90, the magnetic particles "squeeze" the container 140, forcing release of the nerve stimulating drug 142 (preferably in liquid form). Even further, the regulating apparatus 146 may be an electromechanical device incorporating a positive displacement apparatus, such as a membrane or pump, that is selectively activated by the pulse generator 90. The displacement apparatus would force a small volume of the nerve stimulating drug 142 (preferably in liquid form) from the container 140.

The nerve stimulator 130 is implanted as previously described. During use, the pulse generator 90 (FIG. 1) selectively activates the electrode 136 and triggers delivery of the nerve stimulating drug 142 via the regulating means 146. Nerve stimulation by the electrode 136 and the nerve stimulating drug 142 may occur simultaneously or independently.

Figure 4:
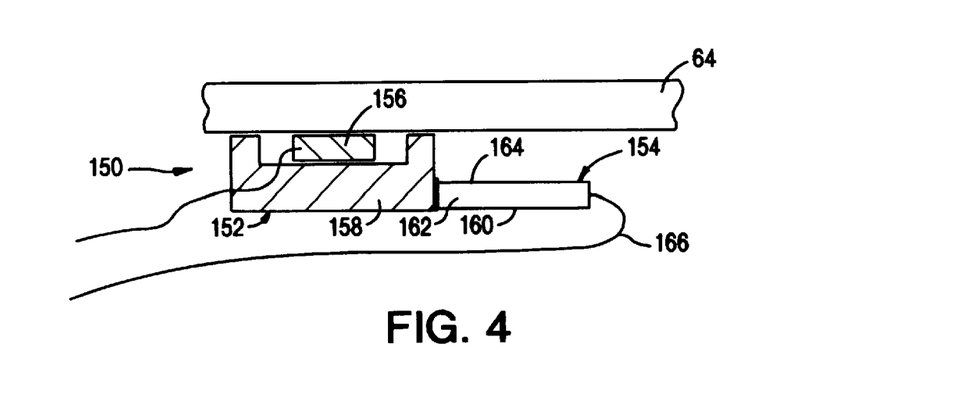
FIG. 4 is a schematic, cross-sectional view of an electrode body and alternative reservoir in accordance with the present invention associated with a nerve.

Yet another alternative embodiment of a nerve stimulator 150 is shown in FIG. 4. The nerve stimulator 150 includes an electrode body 152 operatively associated with a reservoir 154. The electrode body 152 is highly similar to that previously described, and includes an electrode 156 maintained by a base 158. Once again, the base 158 is configured to sustain long-term contact between the electrode 156 and the nerve 64. The electrode 156 is connected to the pulse generator 90 (FIG. 1) by a lead 159.

The reservoir 154 includes a container 160 maintaining a nerve stimulating drug 162 (preferably a veratrum alkaloid) similar to that previously described. The nerve stimulating drug 162 is preferably a solid or semi-solid, and is combined with a polymeric material selected to allow elution of the drug in response to electrical activity. The container 160 defines a delivery surface 164 and positions a lead 166 into contact with the nerve stimulating drug 162. The lead 166 serves as an electrophoretic device (or regulating means) and is electrically connected to the pulse generator 90 (FIG. 1). With this configuration, upon activation by the lead 166, the nerve stimulating drug 162 elutes from the container 160 via the delivery surface 164.

As shown in FIG. 4, the reservoir 154 is operatively associated with the electrode body 152, such as by adhering the container 160 to the base 158. Unlike the nerve stimulator 92 shown in FIG. 2, however, the container 160 is positioned relative to the base 158 such that the delivery surface 164 is slightly spaced from the nerve 64 upon final implant. Thus, the reservoir 154 need not be in direct contact with the nerve 64 for proper nerve stimulation. Importantly, however, the reservoir 154, and in particular the delivery surface 164, is orientated so as to deliver the nerve stimulating drug 162 directly to the nerve 64. With this configuration, the nerve stimulating drug 162 does not interact with collateral nerves or other tissue that might otherwise produce unacceptable side effects.

During use, the nerve stimulator 150 is implanted in conjunction with the pulse generator 90 (FIG. 1) as previously described. Following implantation, the pulse generator 90 serves to selectively activate the electrode 156 and prompt delivery of the nerve stimulating drug 162. More particularly, the pulse generator 90 activates the electrode 156 as previously described. Additionally, the pulse generator 90 prompts release of the nerve stimulating drug 162 from the container 160, via the lead 166. Thus, with the nerve stimulator 160 shown in FIG. 4, the electrode 156 and the nerve stimulating drug 162 can be used independently and/or simultaneously to stimulate the nerve 64. To this end, the pulse generator 90 may include circuitry for correlating electrode activation with drug delivery to develop an overall nerve stimulation therapy, as described in greater detail below.

Figure 5:
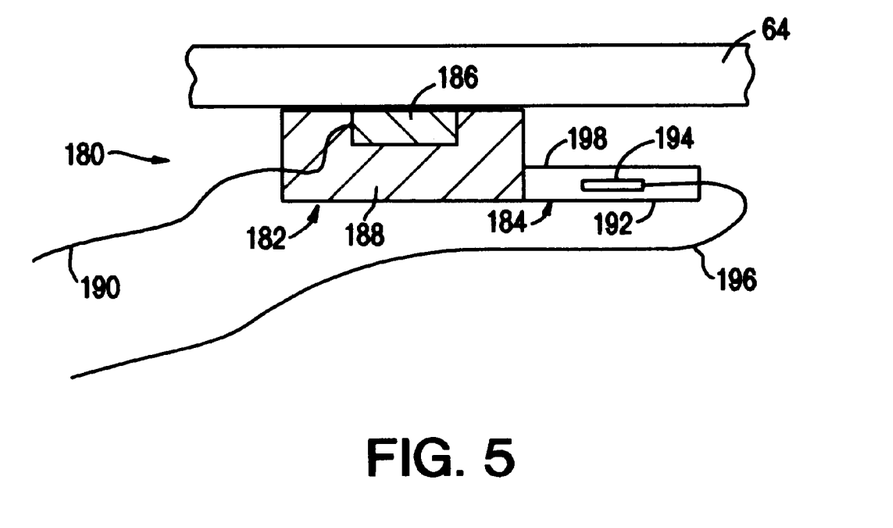
FIG. 5 is a schematic, cross-sectional view of an electrode body and alternative reservoir in accordance with the present invention associated with a nerve.

Yet another alternative embodiment of a nerve stimulator 180 is depicted in FIG. 5. As with previous embodiments, the nerve stimulator 180 includes an electrode body 182 operatively associated with a reservoir 184. The electrode body 182 includes an electrode 186 and a base 188. The base 188 is configured to sustain long-term contact between the electrode 186 and the nerve 64. In this regard, the electrode 186 is connected to the pulse generator 90 (FIG. 1) by a lead 190.

The reservoir 184 is a polymeric matrix layer 192 formed about a heating element 194. The polymeric matrix layer 192 includes a nerve stimulating drug, such as a veratrum alkaloid (as previously described), partially bonded to a polymeric material, such as a silastic medical adhesive. The mixture is molded about the heating element 194 and allowed to cure. After curing, the polymeric matrix layer 192 is attached to the base 188 with a biologically compatible adhesive. Finally, the heating element 194 is electrically connected to the pulse generator 90 (FIG. 1) by a lead 196.

The reservoir 184 is preferably configured such that upon heating by the heating element 194, the polymeric matrix layer 192 releases veratrum alkaloid. To this end, the polymeric matrix layer 192 is preferably configured to provide a delivery surface 198 through which the nerve stimulating drug is released. In this regard, the polymeric matrix 192 may be placed within a container having an open end defining the delivery surface 198.

Prior to use, the nerve stimulator 180 is implanted as previously described. Following implant, the pulse generator 90 (FIG. 1) periodically activates the electrode 186 and/or the heating element 194 to stimulate the nerve 64. Once heated by the heating element 194, the polymeric matrix layer 192 delivers nerve stimulating drug to the nerve 64. Stimulation of the nerve 64 by the electrode 186 and the drug may occur simultaneously or independently.

Figure 6:
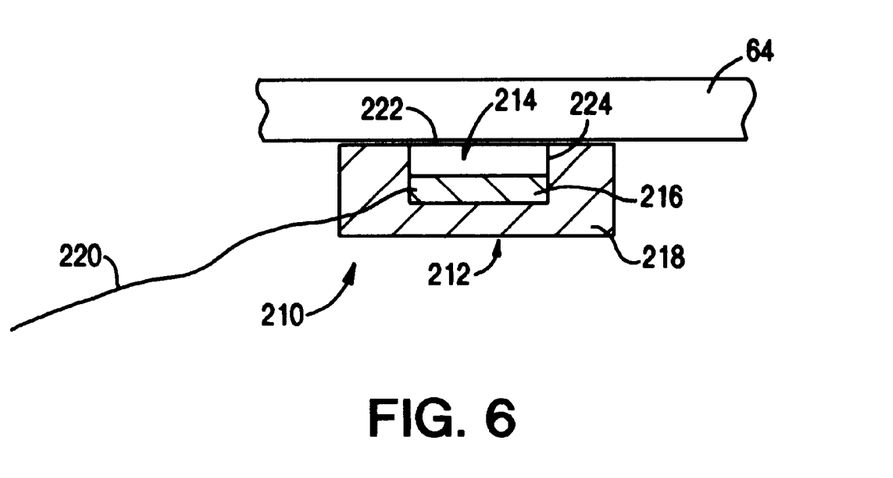
FIG. 6 is a schematic, cross-sectional view of an electrode body and alternative reservoir in accordance with the present invention associated with a nerve.

Yet another alternative embodiment of a nerve stimulator 210 is shown in FIG. 6 in conjunction with the nerve 64. The nerve stimulator 210 includes an electrode body 212 operatively associated with a reservoir 214. As with previous embodiments, the electrode body 210 includes an electrode 216 and a base 218. The base 218 is configured to sustain long-term contact between the nerve 64 and the electrode 216 (via the reservoir 214). The electrode 216 is electrically connected to the pulse generator 90 (FIG. 1) by a lead 220.

The reservoir 214 is polymeric matrix layer 222 maintaining a nerve stimulating drug (preferably a veratrum alkaloid) as previously described. The polymeric matrix layer 222 may be fabricated in a variety of ways, for example by a mixture of a veratrum alkaloid with a polymeric bonding agent. The mixture is molded to the desired shape and allowed to cure. After curing, the polymeric matrix layer 222 is attached to the electrode 216 as shown in FIG. 6. With this configuration, the polymeric matrix layer 222 is effectively impregnated into the electrode body 212. Further, the electrode 216 serves as an electrophoretic mechanism for the delivery of the nerve stimulating drug from a polymeric matrix layer 222.

Prior to use, the nerve stimulator 210 is implanted and secured about the nerve 64 as previously described. Following implant, the pulse generator 90 (FIG. 1) periodically activates the electrode 216, thereby electrically stimulating the nerve 64. Further, activation of the electrode 216 causes the polymeric matrix layer 222 to deliver the nerve stimulating drug to the nerve 64. Notably, because the base 218 surrounds the reservoir 214, the base 218 defines a delivery surface 224 proximate the nerve 64. Thus, the drug is directed into contact solely with the nerve 64, and does not interact with other nerves or tissue.

Figure 7:
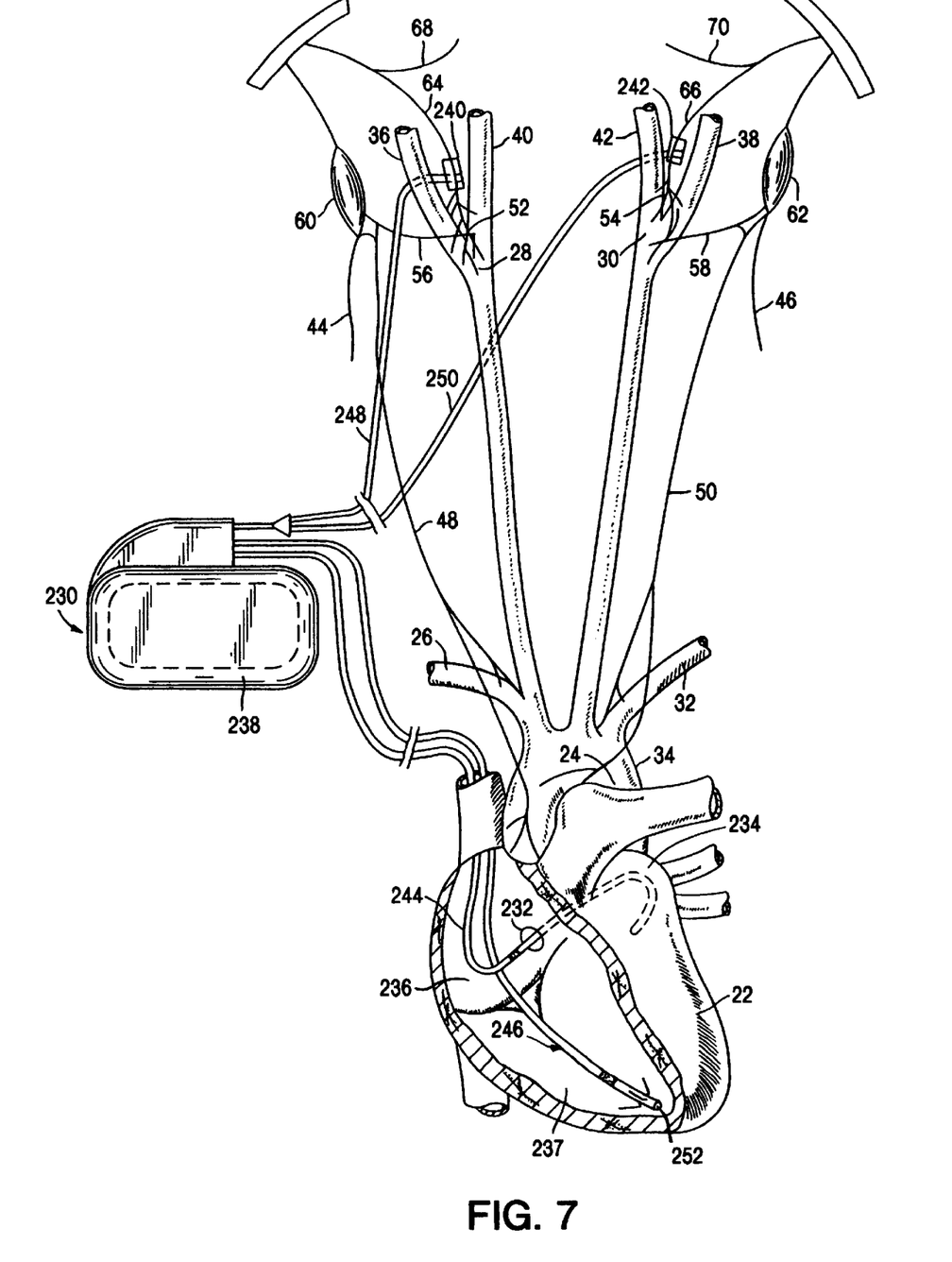
FIG. 7 is a diagrammatic illustration of the heart, its associated blood vessels and nerves, and an alternative implantable medical device in accordance with the present invention coupled thereto.

The medical device 20 (FIG. 1), in conjunction with various nerve stimulator embodiments (FIGS. 2–6) has been described as an open loop system. Alternatively, cardiovascular feedback information may be utilized to better regulate nerve stimulation. With this in mind, an alternative implantable medical device 230 is depicted in FIG. 7 in conjunction with the patient's cardiovascular system previously described with reference to FIG. 1. In FIG. 7, the cutaway view of the heart 22 depicts a coronary sinus opening 232 into the great coronary vein 234 and associated lesser coronary veins into the right atrium 236 and the right ventricle 237.

The medical device 230 generally includes a control device 238, a first nerve stimulator 240, a second nerve stimulator 242 and a cardiovascular sensor system (243 in FIG. 8) including cardiovascular sensors which may be on leads 244, 246. The nerve stimulators 240, 242 may assume any of the forms previously described, and are connected to the control device 238 by leads 248, 250, respectively.

The cardiovascular sensor system 243, and in particular the cardiovascular sensors 244, 246, is configured to provide an indication of performance of the heart 22. For example, in one preferred embodiment, the cardiovascular sensor 244 is a lead body coupled to the control device 238 that extends into the coronary sinus 232 and (optionally) deeply within the coronary vein 234, and preferably carries cardiac performance-related sensors, such as a pH and/or blood oxygen sensor (not shown in FIG. 7). In another preferred embodiment, the cardiovascular sensor 246 is a lead body extending from the control device 238 through the right atrium 236 and into the right ventricle 237. The lead positions an electrode 252 within right ventricle. The electrode 252 senses cardiac activity within the right ventricle 237. Alternatively, the electrode 252 may be positioned in the right atrium to sense atrial activity. Taken in combination, the cardiovascular sensors 244, 246 provide the control device 238 with information indicative of abnormal heart activity. To this end, only one of the cardiovascular sensors on leads 244, 246 need be supplied. Even further, the cardiovascular sensor may assume a wide variety of other forms. For example, the cardiovascular sensor may be a cardiac pacing lead configured to impedance or electrogram signals or sense heart rate; a subcutaneous electrode array for sensing impedance or the cardiac electrogram a blood pressure sensor; an intracardiac pressure sensor; a flow probe placed about an artery; etc. Regardless of exact form, the cardiovascular sensor system 243 provides the control device 238 with a signal indicative of abnormal heart performance.

Figure 8:
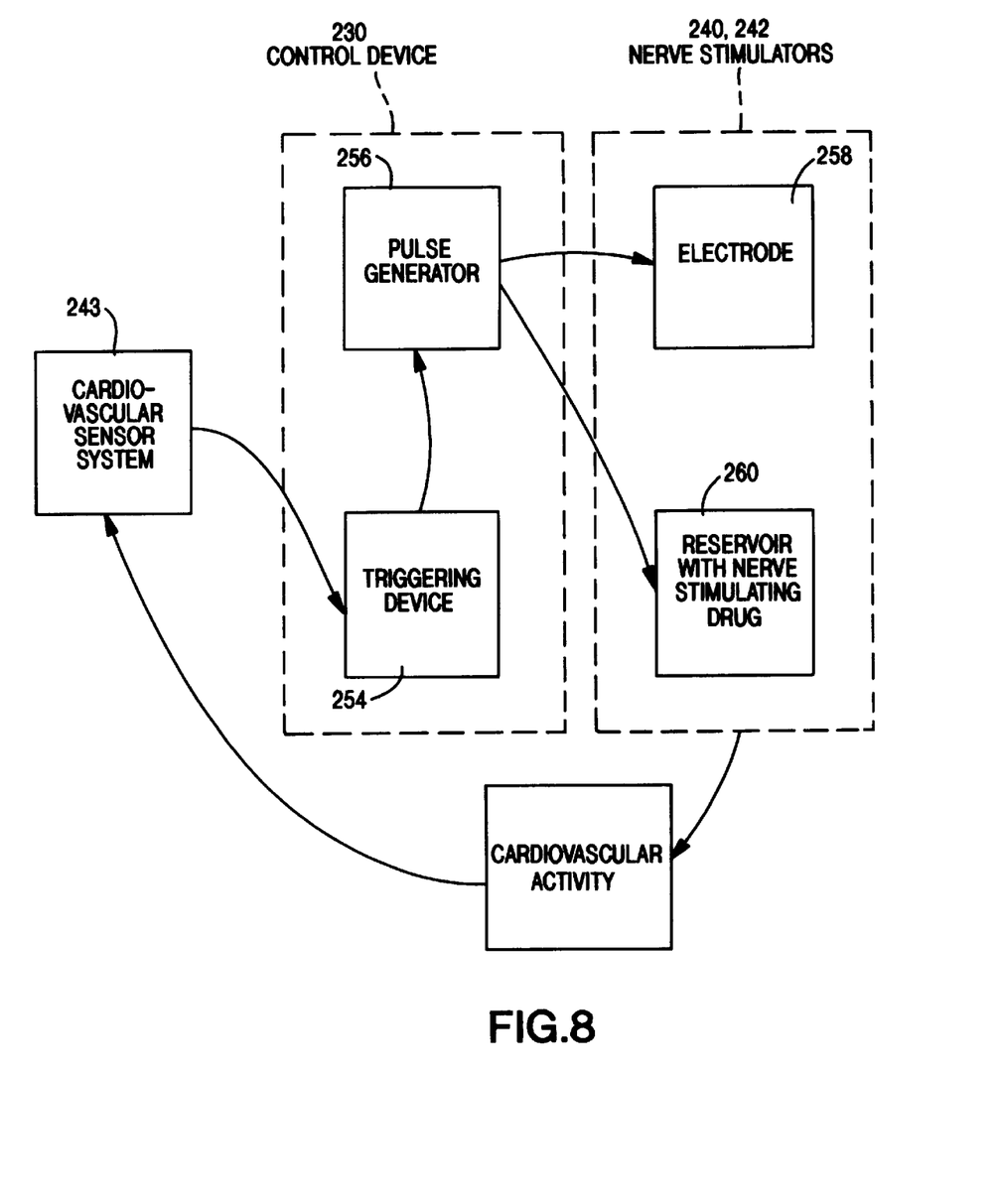
FIG. 8 is a block diagram of the device of FIG. 7.

The above-described medical device 230 provides a closed loop system for treatment of cardiovascular disorders. This relationship is best shown with reference to FIG. 8. As a point of reference, FIG. 8 depicts the control device 238 as incorporating a triggering device 254 and a pulse generator 256. The triggering device 254 is electrically connected to the cardiovascular sensor system 243 (that may include the cardiovascular sensors 244, 246 previously described) and the pulse generator 256. The pulse generator 256, in turn, is electrically connected to the nerve stimulators 240, 242. One example of an acceptable control device 238 is provided in U.S. Pat. No. 5,199,428, the teachings of which are incorporated herein by reference. The nerve stimulators 240, 242 are shown generally in FIG. 8, each including an electrode 258 and a reservoir 260 maintaining a nerve stimulating drug, such as a veratrum alkaloid. The electrode 258 and the reservoir 260 are, in one preferred embodiment, independently activated by the pulse generator 256. Alternatively, the reservoir 260 may be configured to deliver a constant supply of the nerve stimulating drug and would not, therefore, be connected to the pulse generator 256.

Following implant, the cardiovascular sensor system 243, as well as possibly other monitoring systems (see for example U.S. Pat. Nos. 5,313,953; 5,388,578; and 5,411, 031, the teachings of which are incorporated herein by reference) which can monitor cardiovascular condition. At certain times, the cardiovascular sensor system 243 or an associated electrode array may provide signals to a microprocessor circuit controlled by a program in a memory in the cardiovascular sensor system 243 that suggest abnormal heart activity, such as increased heart rate, high blood pressure, arrhythmia, ischemia, etc. using known methods and devices for such monitoring purpose. The cardiovascular sensor system 243 provides a signal indicative of this abnormal cardiovascular activity to the triggering device 254. The triggering device 254 that may also be microprocessor controlled or controlled by a program and control circuit, in turn, signals the pulse generator 256 to selectively activate the nerve stimulators 240, 242. For example, the triggering device 254 may prompt the pulse generator 256 to activate the electrode 258 and the reservoir 260 for a predetermined time period to stimulate the associated nerve. Alternatively, the electrode 258 and the reservoir 260 may be activated sequentially. Following nerve stimulation, a baroreflex occurs or other autonomic action, thereby altering cardiovascular rate and/or other bodily functions so as to control cardiovascular activity to a desired level. Notably, whether nerves other than the carotid sinus nerve are stimulated, for example the median nerves as previously described, the resulting cardiovascular control is of benefit.

Over time, the control device 238 may generate an optimal stimulation therapy for the patient. For example, the control device 238 may include a separate memory and associated circuitry for logging cardiovascular activity both before and after nerve stimulation. To this end, the control device 238 may include a microprocessor-based computer including associated memory and input/output circuitry. Alternatively, the control device 238 may include a programmable logic controller (PLC) or other controller or equivalent circuitry. An example of one acceptable control device is described in U.S. Pat. No. 5,199,428. Based upon the accumulated data, it may be determined that appropriate cardiovascular performance correction is achieved with sequential stimulation of the nerve(s) by the electrode 258 and the nerve stimulating drug. For example, it may be determined that for proper congestive heart failure treatment, the nerve is stimulated once every hour by the electrode 258 for one minute, followed by delivery of the nerve stimulating drug for thirty seconds. The control device 238, via the trigger 254 and the pulse generator 256, prompt the nerve stimulators 240, 242 accordingly. Further, as previously described, the reservoir 260 may be configured to provide a variable delivery rate of the nerve stimulating drug. In this regard, the control device 238 may accumulate data representative of a preferred delivery rate of the drug for achieving optimal cardiovascular performance correction. The control device 238 would then operate so as to prompt this desired delivery rate from the reservoir 260. Alternatively, as opposed to an episodic sensing and control technique, the control device 238 may be configured to continuously monitor cardiovascular performance on a beat-to-beat basis, prompting relatively minor corrections in nerve stimulator 240, 242 activation. Additionally, activation of the nerve stimulators 240, 242 may be synchronized with the cardiac cycle. For example, the nerve stimulators 240, 242 may be prompted to stimulate the nerve(s) at the peak of the QRS complex or other event in the cardiac cycle as described, for example, in U.S. patent application Ser. No. 08/559,957 entitled "Baroreflex Modulation With Carotid Sinus Nerve Stimulation for Treatment of Heart Failure," the teachings of which are incorporated herein by reference.

Even further, the control device 238 may be utilized to avoid overly stimulating the nerve with the electrode 258, thereby minimizing nerve desensitization. For example, an initial activation cycle time for the electrode 258 can be established, and the electrode 258 activated accordingly. The effects of this nerve stimulation on cardiovascular activity are monitored by the cardiovascular sensor system 243 and logged by the control device 238. The nerve stimulating drug is subsequently delivered, and heart activity performance/improvement recorded. Based upon the effectiveness of the drug-induced nerve stimulation, the control device 238 would determine a desired second activation cycle time for the electrode 258; the second activation cycle time being less than the initial activation cycle time. The electrode 258 is then operated in accordance with this second activation cycle time.

The drug delivery neural stimulation device for treatment of cardiovascular disorders of the present invention provides a marked improvement over previous stimulation systems incorporating only an electrode. By stimulating a selected nerve with a nerve stimulating drug, the required level and/or duration of electrode stimulation is greatly reduced, thereby improving battery life and avoiding nerve desensitization. Further, where the nerve stimulating drug is a veratrum alkaloid, direct application of the veratrum alkaloid to the selected nerve avoids the toxicity and side effects encountered with systemic delivery. Finally, by correlating the electrode and drug stimulation, a synergistic, optimized therapy can be achieved.

Although the present invention has been described with reference to preferred embodiments, workers skilled in the art will recognize that changes can be made in form and detail without departing from the spirit and scope of the invention. For example, while the drug maintaining reservoir has been described as incorporating a container and/or a polymeric matrix layer, other configurations are acceptable. For example, the nerve stimulating drug can be formulated into a plug form and secured to the electrode body. Similarly, the reservoir need not be directly connected to the electrode body. Instead, the reservoir may be secured in close proximity to the nerve separate from the electrode body.

What is claimed is:

1. An implantable medical device for enhanced stimulation of a nerve to treat cardiovascular disorders, the device comprising:
   an implantable pulse generator;
   an implantable electrode body including an electrode electrically connected to the pulse generator, the electrode body configured to sustain long-term contact between the electrode and the nerve; and
   a reservoir maintaining a nerve stimulating drug and defining a delivery surface through which the nerve stimulating drug is released from the reservoir;
   wherein the reservoir is operatively controlled by the implantable pulse generator to deliver the nerve stimulating drug directly to the nerve.

2. The device of claim 1, wherein the nerve stimulating drug is a veratrum alkaloid.

3. The device of claim 2, wherein the veratrum alkaloid is selected from the group consisting of protoveratrine and veratridine.

4. The device of claim 1, wherein the reservoir is a polymer matrix containing the nerve stimulating drug.

5. The device of claim 4, wherein the polymer matrix is impregnated into the electrode body.

6. The device of claim 1, wherein the reservoir includes a container having at least one opening defining the delivery surface.

7. The device of claim 1, wherein the delivery surface is a microporous tip.

8. The device of claim 1, wherein the reservoir is associated with the electrode body such that upon final implant of the electrode body, the delivery surface is in close proximity to the nerve.

9. The device of claim 1, further comprising:
   regulating means for regulating release of the nerve stimulating drug from the reservoir in response to physiological feedback.

10. The device of claim 9, wherein the regulating means includes an electrophoretic mechanism formed with the reservoir for initiating delivery of veratrum alkaloid as the nerve stimulating drug.

11. The device of claim 9, wherein the reservoir is configured to deliver the nerve stimulating drug in response to a temperature rise, the regulating means including a heating element contacting the reservoir and connected to the pulse generator for selectively energizing the heating element.

12. The device of claim 9, wherein the regulating means is configured to prompt delivery of the nerve stimulating drug upon activation by the pulse generator, the device further including:
   a triggering device electrically connected to the pulse generator, the triggering device configured to selectively provide an activation signal from the pulse generator to the regulating means.

13. The device of claim 12, further comprising:
   a cardiovascular sensor associated with the heart of the patient for monitoring heart activity and for providing a signal indicative of abnormal cardiovascular activity.

14. The device of claim 13, wherein the triggering device is configured to provide the activation signal in response to the signal indicative of abnormal cardiovascular activity.

15. The device of claim 9, wherein the reservoir is configured to provide a variable delivery rate of the nerve stimulating drug from the reservoir.

16. The device of claim 15, wherein the device further includes a delivery rate circuit for determining a desired delivery rate of the nerve stimulating drug from the reservoir.

17. An improved nerve stimulation system for treatment of cardiovascular disorders including an electrode body having an electrode connected to an implantable pulse generator, the electrode body being configured for implantation within a patient so as to establish long-term contact between the electrode and a nerve, the improvement comprising:

a reservoir maintaining a nerve stimulating drug, the reservoir being operatively associated with the electrode body and configured to deliver the drug directly onto the nerve as controlled by electrical signals provided by the implantable pulse generator.

18. The improvement of claim 17, wherein the nerve stimulating drug is a veratrum alkaloid.

19. The improvement of claim 18, wherein the veratrum alkaloid is selected from the group consisting of protoveratrine and veratridine.

20. The improvement of claim 17, wherein the reservoir is configured to allow constant elution of the nerve stimulating drug upon implant.

21. The improvement of claim 17, wherein the system includes at least one sensor for sensing physiological signals, and the reservoir is configured to control delivery of the nerve stimulating drug based on physiological feedback provided by the at least one sensor.

22. The improvement of claim 21, wherein the nerve stimulating drug is formulated to elute a drug in response to a temperature rise, the reservoir including a heating element electrically connected to the pulse generator for causing a temperature rise.

23. The improvement of claim 21, wherein the reservoir includes a container maintaining the nerve stimulating drug in liquid form and a positive displacement mechanism, the positive displacement mechanism configured to selectively force the nerve stimulating drug from the container.

24. A method for improved neural stimulation to treat cardiovascular disorders, the method comprising:

providing a control device;

stimulating a selected nerve with an electrode activated by the control device; and stimulating the nerve with a drug delivered from a reservoir maintaining the drug, the reservoir being implanted in close proximity to the nerve and activated to deliver drugs by the control device.

25. The method of claim 24, wherein stimulating the nerve with a drug includes delivering a veratrum alkaloid to the nerve.

26. The method of claim 24, further including:

associating the electrode and the reservoir with a carotid sinus nerve.

27. The method of claim 24, wherein the nerve is periodically stimulated by the electrode and the drug.

28. The method of claim 24, wherein the reservoir is configured to selectively deliver the drug, the method further comprising:

correlating the delivery of the drug with activation of the electrode to generate a nerve stimulation therapy.

29. The method of claim 28, wherein correlating delivery of the drug includes:

establishing an activation cycle time for the electrode;

delivering the drug;

determining a level of nerve stimulation caused by the drug; and altering the activation cycle time for the electrode based upon the level of nerve stimulation caused by the drug.

30. The method of claim 24, wherein the reservoir is configured to selectively deliver the drug, the method further comprising:

controlling delivery of the drug from the reservoir based on cardiovascular feedback information received by the control device.

31. The method of claim 30, wherein the control device includes a triggering device connected to the reservoir, and further wherein controlling delivery of the drug includes:

signaling the reservoir with the triggering device to prompt delivery of the drug.

32. The method of claim 30, wherein a cardiovascular sensor is provided for sensing abnormal cardiovascular activities of the patient and generating a signal indicative of an abnormal cardiovascular activity, and further wherein controlling delivery of the drug includes:

activating the reservoir in response to the signal.

33. The method of claim 30, wherein the reservoir is configured to provide a variable delivery rate, and further wherein controlling delivery of the drug includes:

determining a desired rate of delivery of the drug; and controlling the reservoir to deliver the drug at the desired delivery rate.

* * * * *